United States Patent [19]
Mishiro et al.

[11] Patent Number: 5,176,994
[45] Date of Patent: Jan. 5, 1993

[54] NON-A, NON-B HEPATITIS VIRUS GENOME RNA, CDNA AND VIRUS ANTIGEN PROTEIN

[75] Inventors: Shunji Mishiro; Tetsuo Nakamura, both of Tokyo, Japan

[73] Assignee: Immuno Japan Inc., Tokyo, Japan

[21] Appl. No.: 700,246

[22] Filed: May 15, 1991

Related U.S. Application Data

[60] Division of Ser. No. 540,604, Jun. 19, 1990, Pat. No. 5,077,193, and a continuation-in-part of Ser. No. 451,968, Dec. 19, 1989, abandoned.

[30] Foreign Application Priority Data

Dec. 21, 1988 [JP] Japan ................................ 63-322547

[51] Int. Cl.⁵ ..................... C12Q 1/70; G01N 33/53; G01N 33/569; C07K 7/04
[52] U.S. Cl. ........................................ 435/5; 435/7.1; 435/7.92; 435/7.94; 530/324; 436/820; 436/518; 436/513; 436/536
[58] Field of Search ................. 435/5, 7.1, 7.92, 7.93, 435/7.94; 436/513, 538, 542, 518, 820, 536; 530/324

[56] References Cited

U.S. PATENT DOCUMENTS 4,673,634  6/1987  Seto et al. .............................. 435/5

OTHER PUBLICATIONS

Wide, L. in Principles of Competitive Protein Binding Assays (ed.) W. O. Odell & P. Franchimont (1983) New York: John Wiley & Sons. pp. 243-254.

*Primary Examiner*—Robert A. Wax
*Assistant Examiner*—Gabriele E. Bugaisky
*Attorney, Agent, or Firm*—Beveridge, DeGrandi & Weilacher

[57] ABSTRACT

Non-A, Non-B Hepatitis Virus Genome RNA is disclosed along with cDNA and Virus Antigen Protein.

5 Claims, 3 Drawing Sheets

NON-A, NON-B HEPATITIS VIRUS GENOME RNA, CDNA AND VIRUS ANTIGEN PROTEIN

INTRODUCTION AND BACKGROUND

This application is a division of application Ser. No. 07/540,604, filed Jun. 19, 1990, now U.S. Pat. No. 5,077,193 and a continuation-in-part application of patent application Ser. No. 07/451,968, filed Dec. 19, 1989, now abandoned which is relied on and incorporated herein.

This invention relates to Non-A, Non-B hepatitis virus genome RNA, its cDNA as well as its virus antigen protein.

Viral hepatitis is divided approximately into two categories; enterically transmitted hepatitis and parenterally transmitted (blood-borne) hepatitis. Hepatitis A virus in the former and hepatitis B virus in the latter have been isolated as causative agents and their virological properties have been elucidated. As the results, diagnosis of and preventive measures against infection with those viruses have been established and diseases caused by them are held closely under control.

Parenterally transmitted Non-A, Non-B hepatitis (PT-NANB) is said to be about 95% of post-transfusion hepatitis cases in Japan, however, nothing has been confirmed of its causative virus except for its experimental transmission to chimpanzees as the only susceptive animals other than human beings. Almost all attempts made so far by various researchers have failed in identification of the causative agent virus because of the poor reproducibility of the reported results.

Very recently Chiron's scientists reported hepatitis C virus (HCV) as a causative agent of PT-NANB. Its genomic structure is said to resemble that of flavi viruses and an immunosassay using antigenic polypeptide deduced from HCV genomic sequence is, reportedly, capable of detecting antibodies highly associated with PT-NANB. But, virologically there is no evidence that HCV is the PT-NANB agent.

Arima also reported the nucleotide sequences of cDNA clones derived from PT-NANB patients' plasma after Chiron's disclosure of HCV genome. The nucleotide sequences of Chiron's, Arima's and the current invention are mutually independent, i.e., there is no homology among any pair of them.

Applicants have been strenuously conducting research in Non-A, Non-B hepatitis and have succeeded in isolating a cDNA clone very closely associated with PT-NANB. There is a clear association between the nucleotide sequence of the cDNA clone and PT-NANB; nucleotide-hybridization assay can detect virus and an immunoassay using polypeptide deduced from the cDNA can detect antibodies in PT-NANB infected subjects. It has further been found that they are effective in diagnosis, prevention and therapy of PT-NANB as materials for diagnostic test kits or immunogens.

SUMMARY OF INVENTION

One feature of the present invention resides in providing a PT-NANB virus genome RNA having the following base sequence;

```
5' UGAUAAAAUAAGCCAGGG
UGAUUCUUAAUUUUCAGUCU
GAAGUCUUUUUUCCCCUCCC
AGUCCAGUCUCCUCAUUUAC
UAGGGUCAGCAGGGAGAGAG
AGAAGGUCAGCUGUGAAUGU
UUCCCCUCCCCAGAAUGGGG
UGGGCUGGUCCUGAGUUGCA
GCUCGGGGUGGGGGACGUGA
ACCAGCC 3'
```

(hereinafter called "N-4880-RNA");

Another feature of the inventive residues in complementary DNA to PT-NANB virus genome RNA having the following base sequence;

```
5' GGCTGGTTCACGTCCCCC
ACCCCGAGCTGCAACTCAGG
ACCAGCCCACCCCATTCTGG
GGAGGGGAAACATTCACAGC
TGACCTTCTCTCTCTCCCTG
CTGACCCTAGTAAATGAGGA
GACTGGACTGGGAGGGGAAA
AAAGACTTCAGACTGAAAAT
TAAGAATCACCCTGGCTTAT
TTTATCA 3'
```

(hereinafter called "N-4880-cDNA-T3"); and

A still further feature of the present invention resides in homologous DNA to PT-NANB virus genome RNA having the following base sequence;

```
5' TGATAAAATAAGCCAGGG
TGATTCTTAATTTTCAGTCT
GAAGTCTTTTTTCCCCTCCC
AGTCCAGTCTCCTCATTTAC
TAGGGTCAGCAGGGAGAGAG
AGAAGGTCAGCTGTGAATGT
TTCCCCTCCCCAGAATGGGG
TGGGCTGGTCCTGAGTTGCA
GCTCGGGGTGGGGGACGTGA
ACCAGCC 3'
```

(hereinafter called "N-41880-cDNA-T7"); and

Yet another feature of the invention resides in a PT-NANB virus antigen protein having the following amino acid residue sequence;

Leu—Val—His—Val—Pro
—His—Pro—Glu—Leu—Gln
—Leu—Arg—Thr—Ser—Pro
—Pro—His—Ser—Gly—Glu
—Gly—Lys—His—Ser—Gln
—Leu—Thr—Phe—Ser—Leu
—Ser—Leu—Leu—Thr—Leu
—Val—Asn—Glu—Glu—Thr
—Gly—Leu—Gly—Gly—Glu
—Lys—Arg—Leu—Gln—Thr
—Glu—Asn (hereinafter called "N-4880-P")

BRIEF DESCRIPTION OF FIGURES

FIGS. 2 2A and 2B is a photograph and show antibody response of a chimpanzee infected with PT-NANB hepatitis along its time-course by antibody detection method used for the data in FIG. 1.

DETAILED DESCRIPTION OF INVENTION

Figure 1:
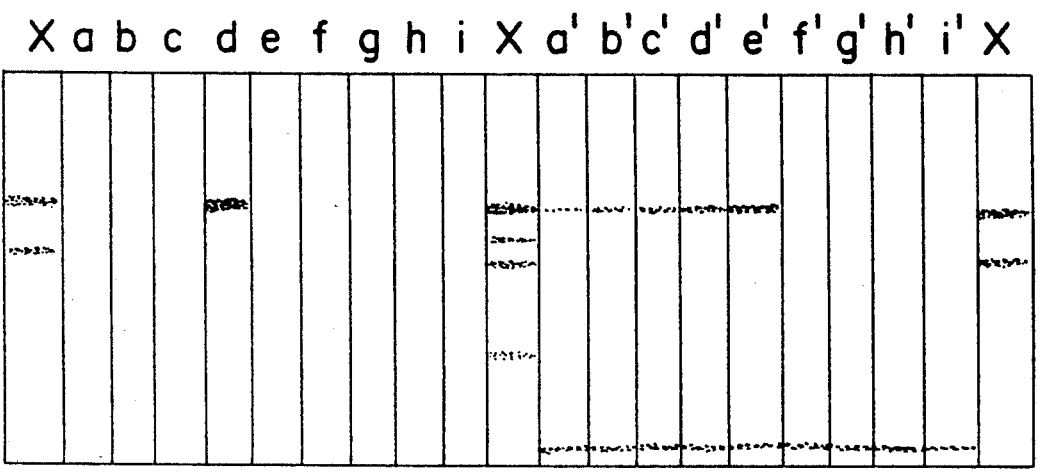
FIG. 1 is a photograph and shows detection of antibody against PT-NANB associated protein antigen (N-4880-P) by Western blotting.

Applicants have refined and produced the nucleic acid and antigen protein as described herein in the following way.

(1) Experimental infection of chimpanzees with PT-NANB. To reproduce PT-NANB hepatitis, chimpanzees were intravenously injected with human serum known to have caused post transfusion hepatitis. Since this hepatitis did not show antigen-antibody response specific to hepatitis A or hepatitis B, it was concluded to be Non-A, Non-B hepatitis. Moreover, because of the ultrastructural changes characteristic to PT-NANB noted in the cytoplasm of hepatocytes, it was diagnosed PT-NANB.

(2) Extraction of nucleic acid from chimpanzee plasma.

6 ml of chimpanzee plasma which showed PT-NANB virus titre higher than $10^7$ CIU/ml was layered on top of 4 ml of 20% sucrose and centrifuged on the SW40 rotor (Beckman) centrifuge at 38,000 rpm for 5.4 hours at 4° C. After addition to its precipitate of SDS and Proteinase K (2% and 1 mg/ml respectively) and, then, overnight incubation at 37° C., nucleic acids extracted from phenol of pH 8.5 was precipitated by ethanol.

(3) cDNA synthesis.

The nucleic acid obtained under (2) above was heated at 70° C. for 1 minute and had added thereto oligo dT and random hexamer as primers and had further added thereto 4 types of dNTP and reverse transcriptase for reaction to synthesize the primary cDNA chain. Detailed reaction conditions were set according to the protocol provided to the cDNA synthesis kit (Amersham, England). According to the protocol of the above kit, the secondary cDNA strand was synthesized by ribonuclease H (RNase H) and DNApol.

(4) Phage library of cDNA.

The double stranded cDNA obtained under (3) above was, after treatment with EcoR1 methylase, provided with EcoR1 linker at both ends, ligated with Lamda-gt11 DNA at its EcoR1 site, then, packaged in the phage particles and infected to *E. coli* Y1090 to obtain a recombinant phage library of $2 \times 10^6$ PFU. The protocol of the Lamda-gt 11 cloning kit (Amersham, England) was followed in the experiment.

(5) Screening of phage library.

10,000 PFU of the phage library prepared in (4) above was plated onto the LB agar in $90 \times 90$ mm disc and when placques were formed, they were covered with the nitrocellulose membrane impregnated with IPTG for incubation for 2 hours at 37° C. After incubation, the membrane was removed, and washed with the buffer solution and blocked for 1 hour at room temperature with the buffer solution containing 40% fetal calf serum and 0.05% Tween 20. As the primary antibody, 50 times diluted sera of human and chimpanzee known to be PT-NANB virus carriers were used and the membrane was immersed in each serum for overnight incubation at 4° C. After washing with the buffer solution containing 0.05% Tween 20, secondary antibody (peroxidase labeled mixture of antibodies against human IgG, IgM and IgA) was added and incubated for 30 minutes at room temperature. After washing with the buffer solution containing 0.05% Tween 20, DAB, Ni, Co and $H_2O_2$ were added for color reaction.

(6) Preparation of lysogen.

Antigen positive phage prepared under (5) above were isolated and *E. coli* Y1089 was infected with it. The lysogen was prepared according to the method described in "Constructing and screening cDNA Libraries in Lamda gT11", Thanh V, Huynh, et al, DNA Cloning, Volume 1, a practical approach edited by D. M. Clover, P49–78, IRL Press, Oxford, 1985.

(7) Purification of β-galactosidase fusion protein.

Lysate was made from the lysogen prepared under (6) above and was passed through an affinity column coated with anti-β-galactosidase antibody and the column was treated with 4.5M $MgCl_2$ to elute purified β-galactosidase fusion protein.

(8) Subcloning and sequencing of cDNA.

Phage DNA of an antigen positive placque obtained under (5) above was purified and digested with EcoR1 to take out cDNA and subcloned to the EcoR1 site of Phagescript TM (STRATAGENE-USA) and sequenced with the Sanger method.

The RNA probe having homologous sequence to N-4880-cDNA-$T_3$ hybridized successfully with the virus genome RNA, while the probe having complementary sequence to N-4880-cDNA-$T_3$ did not. Thus, the genome RNA was concluded to be single stranded and have the same polarity as N-4880-cDNA-$T_7$.

Since the Open Reading Frame (ORF) starting from the third base and terminating at the stop condon at the 159–161th base of N-4880-cDNA-$T_3$ forms fusion protein with lac operon of Lamda gt11 phage used for expression of the protein, this ORF was translated to deduce the amino acid sequence of N-4880-P.

The present invention is illustrated by the examples described below which relate to application of the invention.

(9) Detection of antibody to PT-NANB virus antigen protein (N-4880-P).

After treatment for 5 minutes at 100° C. in the presence of 1% SDS and 1% 2ME (2-Mercaptoethanol), β-galactosidase fusion protein obtained under (7) above was subjected to SDS-PAGE (8%) and was transferred to the nitrocellulose membrane (Western blotting). After washing and drying, the membrane was shredded and blocked with 40% fetal calf serum, and those shreds were applied with antibody samples as the primary antibody and incubated overnight at 4° C. After washing with the buffer solution containing the surfactant 0.05% Tween 20, and immersion in biotinylated anti-human IgG or anti-human IgM for 30 minutes incubation at the room temperature, they were applied with the complex of avidin and biotinylated peroxidase, then incubated for 45 minutes at room temperature. For color reaction, Konica Immunostain TM (Konica, Japan) or DAB, NI, Co, $H_2O_2$ method was used. (FIG. 1) FIG. 1 shows an example of Western blot analysis of PT-NANB antigen protein (N-4880-P) fused with β-galactosidase. Primary Antibodies (Test Samples);

a-a': Chimpanzee plasma before Non-A, Non-B hepatitis infection—(1)

b-b': Chimpanzee plasma before Non-A, Non-B hepatitis infection—(2)

c-c': Chimpanzee plasma before Non-A, Non-B hepatitis infection—(3)

d-d': Chimpanzee plasma with persistent Non-A, Non-B hepatitis infection—(1)
e-e': Human plasma with persistent Non-A, Non-B infection
f-f': Chimpanzee plasma with persistent Non-A, Non-B hepatitis infection—(2)
g-g': Chimpanzee plasma after recovery from Non-A, Non-B hepatitis—(1)
h-h': Chimpanzee plasma after recovery from Non-A, Non-B hepatitis—(2)
i-i': Chimpanzee plasma after recovery from Non-A, Non-B hepatitis—(3)
X: Anti-$\beta$-glaactosidase rabbit anti-serum
Secondary Antibodies
a-i: anti-human IgM
a'-i': anti-human IgG
X: anti-rabbit Ig As shown in the FIG. 1, highly intense immunostained bands of the fusion protein were noted in lanes d and e'. That is, with persistent Non-A, Non-B infection hosts, antibody against N-4880-P is positive. This suggests that N-4830-P is virus core (gag) protein rather than virus envelope (env) protein.

Figure 2:
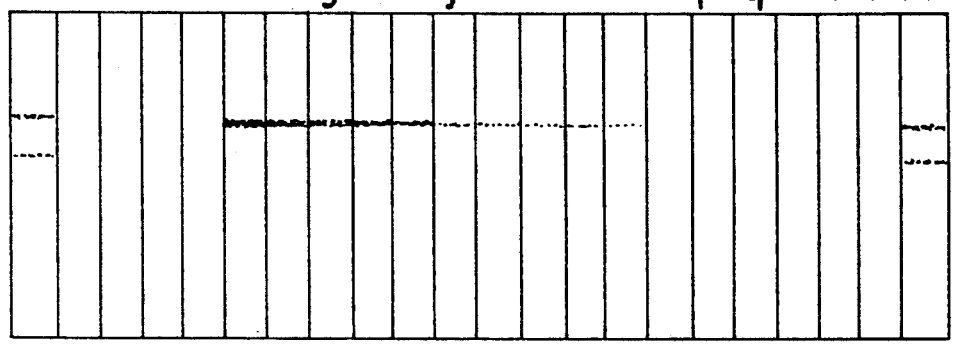
Figure 2:
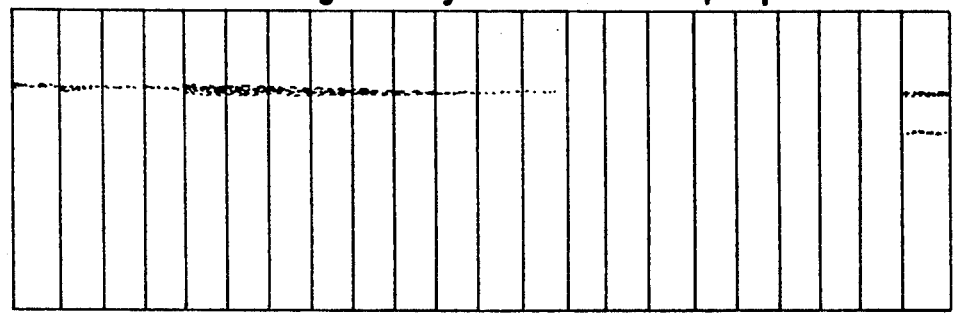

Second example of the Western blot analysis described in (9) is shown in FIG. 2.
Primary Antibodies (Test Samples)
a-t, a'-t': Same chimpanzee plasma as that used in d-d' in FIG. 1 was taken along its time course of infection with PT-NANB hepatitis and was diluted 20 times.
a: Before infection
b: 4 weeks after infection
c: 5 weeks after infection
d: 6.5 weeks after infection
e: 7 weeks after infection
f: 8 weeks after infection
g: 9 weeks after infection
h: 10 weeks after infection
i: 12 weeks after infection
j: 14 weeks after infection
k: 15.5 weeks after infection
l: 21 weeks after infection
m: 23 weeks after infection
n: 25 weeks after infection
o: 26 weeks after infection
p: 29 weeks after infection
q: 32 weeks after infection
r: 40 weeks after infection
s: 42 weeks after infection
t: 45 weeks after infection
X: Anti-$\beta$ galactosidase rabbit anti-serum
Secondary Antibodies
(A) Anti-human IgM
(B) Anti-human IgG
X: Anti-rabbit Ig As shown in the FIGURE, the antibody against Non-A, Non-B associated antigen protein (N-4880-P) of this invention did not exist in the plasma of the chimpanzee before its infection with PT-NANB hepatitis and was found to appear at approximately 7 weeks after infection.

Figure 3:
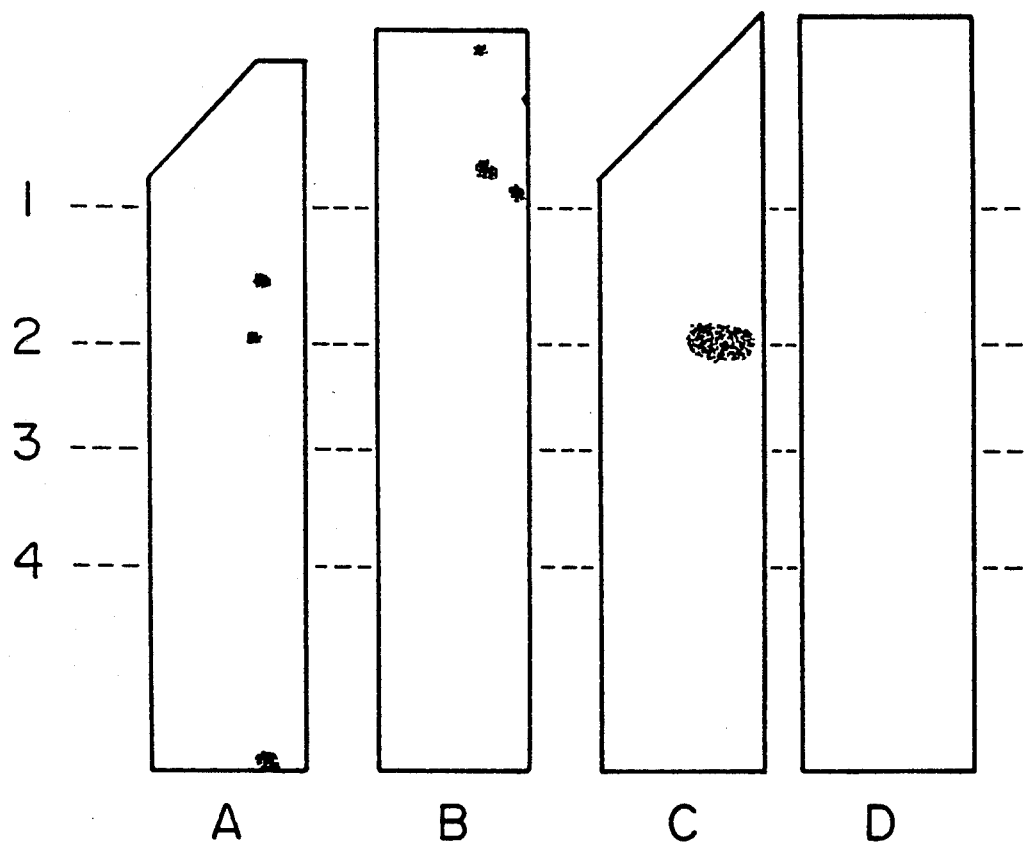
FIG. 3 is a photograph and shows detection of the virus genome RNA by hybridization method.

(10) Hybridization assay using the cDNA as probe
Strand specific RNA probes were made by transcribing the recombinant phagescript DNA utilizing $T_3$ or $T_7$ promotors which reside at opposite sides of the inserted cDNA.
FIG. 3 shows an example of hybridization using radio isotope labeled probe derived from N-4880-cDNA obtained in (10) above. Same plasma as used in the lane d, d' in FIG. 1 was centrifuged in CsCl and fractions with specific gravities 1.22 (1), 1.19 (2), 1.16 (3) and 1.13 (4) were obtained. After dilution of each fraction with the buffer solution, particles of each fraction were precipitated, its nucleic acid was extracted by phenol after digestion with SDS and Proteinase K, then, slot blotted on nylon membrane after denaturization by NaOH (panel A and B), or formaldehyde (panel C and D). As probes for hybridization, RNA probe (A and C) made from Phagescript subclone of N-4880-cDNA by T3 promotor and RNA probe (B and D) made by T7 promotor were used.

As noted in FIG. 3, blot 2 of the panel C alone showed high signal. This suggests that the virus genome of Non-A, Non-B hepatitis is single stranded RNA and is complementary to N-4880-cDNA-$T_3$, and that it is antisense strand. This further suggests that the particle (virus) including the genome RNA has the specific gravity of 1.19 g/cm$^2$ which is proven by the infection experiment with chimpanzees.

of a type of blood-borne Non-A, Non-B hepatitis, applicants have determined that its causative virus has a specific gravity of 1.19 g/cm$^2$ in a cesium chloride density gradient, and that the type of genome RNA is single stranded having (−) polarity. In addition, applicants have determined partial nucleotide sequence of the genome RNA, nucleotide sequence of complementary cDNA and antigen protein produced by its translation. RNA, cDNA and protein made available by this invention are useful in the manufacture of PT-NANB hepatitis diagnostic kit, medicine and vaccine.

The present invention also concerns diagnostic test kits for detecting antibodies against PT-NANB in biological samples, including for example blood and serum samples. Design of the immunoassay is subject to a great deal of variation, and a variety of these are known in the art. For example, the immunoassay may utilize one viral antigen, for example N-4880-P; alternatively, the immunoassay may use a combination of viral antigens. Protocols may, for example, use solid supports such as polyvinyl microtiter plates or beads, or may be by immunoprecipitation. The presence of IgG and/or IgM antibodies to PT-NANE antigens such as N-4880-P can be detected using conventional immunoassays known in the art. These include enzyme-linked immunosorbent assay (ELISA), hemagglutination and radioimmunoassay (RIA) techniques. Most assays involve the use of labeled antibody or polypeptide; the labels may be, for example, fluorescent, chemiluminescent, radioactive, or dye molecules. These labels have been extensively reported in the patent and technical literature.

Kits suitable for immunodiagnosis and containing the appropriate labeled reagents are constructed by packaging the appropriate materials, including N-4880-P in suitable containers, along with the remaining reagents and materials required for the conduct of the assay, as well as a suitable set of assay instructions.

The present invention also concerns diagnostic test kits for detecting the presence of PT-NANB in biological samples, including for example blood and serum samples. Use of the disclosed PT-NANB single stranded DNA or RNA is useful as a probe in identification of the viral agent, detection of the virus in diseased individuals, and detection of PT-NANB RNA. Conventional probe techniques are well known in the art. The probes can be labeled. Suitable labels, and methods for labeling probes are known in the art, and include, for example, radioactive labels, fluorescent probes, and chemiluminescent probes.

The probes can be packaged into diagnostic kits. Diagnostic kits include the probe DNA or RNA, which may be labeled; alternatively the probes may be unlabeled and the ingredients for labeling may be included in the kit. The kit may also contain other suitably packaged reagents and materials needed for the particular protocol, for example, standards, as well as instructions for conducting the test.

The present invention further concerns a prophylactic method of protecting a patient against becoming infected with PT-NANB. Antibody to PT-NANB antigens can be given to susceptible persons for a passive immunoprophylaxis and PT-NANB antigens are used as a vaccine for an active immunoprophylaxis. Antibodies against PT-NANB antigens can be produced by conventional methods known to the art. The active component of the vaccine can be employed with a physiologically acceptable diluent. The vaccine may be linked to a carrier such as a protein carrier, such as tetanus toxoid, keyhole limpet hemocyanin, or another protein or polypeptide which would elicit a good response in the host; non-protein carriers such as polysaccharides, organic polymers, inorganic polymers, lipids, lipid vesicles and liposomes may also be used. The vaccine can be used with or without an adjuvant. Conventional adjuvants include aluminum hydroxide (alum), murammyl dipeptide, any acceptable oil and water combination. The amount of the adjuvant which is employed will vary widely depending on the nature of the adjuvant. Such carriers, adjuvants and the like are known in the art.

The vaccine can be administered parenterally, by injection, for example, either subcutaneously or intramuscularly. Additional formulations which are suitable for other modes of administration include suppositories and, in some cases, oral formulations. The vaccine can be administered in such amount as will be prophylactically and/or therapeutically effective. The quantity to be administered depends on the subject to be treated, capacity of the subject's immune system to synthesize antibodies, and the degree of protection desired. The vaccine may be given in a single dose schedule or in a multiple dose schedule. The hepatitis vaccine of the present invention is recommended for all persons at risk of developing non-A, non-B hepatitis and particularly those at especially high risk.

The non-A, non-B hepatitis vaccine of the present invention may contain a peptide, either a synthetic peptide (peptide produced by assembling individual amino acids by chemical means or by expression vectors (DNA route)) or a peptide derived from natural sources. The vaccine can contain PT-NANB antigens such as N-4880-P. Any analog of PT-4880-P of the present invention involving amino acid deletions, amino acid replacements, or amino acid additions can be utilized, so long as the sequences elicit antibodies recognizing PT-4880-P.

U.S. Pat. No. 4,847,080 is incorporated by reference to illustrate techniques and methods that are well known in the art.

Further variations and modifications of the foregoing will be apparent to those skilled in the act and are intended to be encompassed by the claims appended hereto.

We claim:

1. Non-A, Non-B hepatitis virus antigen protein having the following amino acid sequence:

Leu—Val—His—Val—Pro
—His—Pro—Glu—Leu—Gln
—Leu—Arg—Thr—Ser—Pro
—Pro—His—Ser—Gly—Glu
—Gly—Lys—His—Ser—Gln
—Leu—Thr—Phe—Ser—Leu
—Ser—Leu—Leu—Thr—Leu
—Val—Asn—Glu—Glu—Thr
—Gly—Leu—Gly—Gly—Glu
—Lys—Arg—Leu—Gln—Thr
—Glu—Asn

2. A Non-A, Non-B hepatitis diagnostic reagent test kit comprising a polypeptide having the following amino acid sequence:

Leu—Val—His—Val—Pro
—His—Pro—Glu—Leu—Gln
—Leu—Arg—Thr—Ser—Pro
—Pro—His—Ser—Gly—Glu
—Gly—Lys—His—Ser—Gln
—Leu—Thr—Phe—Ser—Leu
—Ser—Leu—Leu—Thr—Leu
—Val—Asn—Glu—Glu—Thr
—Gly—Leu—Gly—Gly—Glu
—Lys—Arg—Leu—Gln—Thr
—Glu—Asn.

3. An immunoassay for detecting antibodies directed against non-A, non-B hepatitis antigens comprising:

(a) incubating a sample suspected of containing anti-non-A, non-B hepatitis antibodies with a non-A, non-B hepatitis antigen under conditions which allow the formation of an antibody-antigen complex; and (b) detecting the antibody-antigen complex containing the probe antigen; wherein the non-A, non-B hepatitis antigen is a polypeptide having the following amino acid sequence:

Leu—Val—His—Val—Pro
—His—Pro—Glu—Leu—Gln
—Leu—Arg—Thr—Ser—Pro
—Pro—His—Ser—Gly—Glu
—Gly—Lys—His—Ser—Gln
—Leu—Thr—Phe—Ser—Leu
—Ser—Leu—Leu—Thr—Leu
—Val—Asn—Glu—Glu—Thr
—Gly—Leu—Gly—Gly—Glu
—Lys—Arg—Leu—Gln—Thr
—Glu—Asn.

4. A non-A, non-B hepatitis diagnostic test kit for analyzing samples for the presence of antibodies directed against a non-A, non-B hepatitis antigen comprising labeled anti-human IgG and a non-A, non-B hepatitis antigen protein attached to a solid substrate, wherein said non-A, non-B hepatitis antigen protein has the following amino acid sequence:

Leu—Val—His—Val—Pro
—His—Pro—Glu—Leu—Gln
—Leu—Arg—Thr—Ser—Pro
—Pro—His—Ser—Gly—Glu
—Gly—Lys—His—Ser—Gln
—Leu—Thr—Phe—Ser—Leu
—Ser—Leu—Leu—Thr—Leu
—Val—Asn—Glu—Glu—Thr
—Gly—Leu—Gly—Gly—Glu
—Lys—Arg—Leu—Gln—Thr
—Glu—Asn.

5. A non-A, non-B hepatitis diagnostic test kit for analyzing samples for the presence of antibodies directed against a non-A, non-B hepatitis antigen comprising labeled anti-human IgM and a non-A, non-B hepatitis antigen protein attached to a solid substrate, wherein said non-A, non-B hepatitis antigen protein has the following amino acid sequence:

Leu—Val—His—Val—Pro
—His—Pro—Glu—Leu—Gln
—Leu—Arg—Thr—Ser—Pro
—Pro—His—Ser—Gly—Glu
—Gly—Lys—His—Ser—Gln
—Leu—Thr—Phe—Ser—Leu
—Ser—Leu—Leu—Thr—Leu
—Val—Asn—Glu—Glu—Thr
—Gly—Leu—Gly—Gly—Glu
—Lys—Arg—Leu—Gln—Thr
—Glu—Asn.

* * * * *